(12) United States Patent
Langer et al.

(10) Patent No.: US 6,849,272 B1
(45) Date of Patent: *Feb. 1, 2005

(54) ENDOSOMOLYTIC AGENTS AND CELL DELIVERY SYSTEMS

(75) Inventors: Robert S. Langer, Newton, MA (US); David A. Putnam, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,552

(22) Filed: Apr. 20, 2000

Related U.S. Application Data

(60) Provisional application No. 60/130,362, filed on Apr. 21, 1999.

(51) Int. Cl.$^7$ ................................................. A61K 9/14
(52) U.S. Cl. ........................ 424/489; 424/491; 424/450; 514/44
(58) Field of Search ................................. 424/486, 489, 424/491, 450, 497, 468, 484; 435/320.1, 325, 455, 458; 514/44

(56) References Cited

U.S. PATENT DOCUMENTS

| | | | | |
|---|---|---|---|---|
| 5,633,234 A | * | 5/1997 | August et al. ................ | 514/44 |
| 5,762,918 A | * | 6/1998 | Thorpe ..................... | 424/78.17 |
| 5,830,730 A | * | 11/1998 | German et al. .......... | 435/172.3 |
| 6,218,370 B1 | * | 4/2001 | Bischoff et al. .............. | 514/44 |
| 6,267,987 B1 | * | 7/2001 | Park et al. ................... | 424/486 |
| 2001/0006817 A1 | * | 7/2001 | Pack et al. .................. | 435/440 |
| 2003/0002841 A1 | * | 1/2003 | Trubetskoy ................ | 424/486 |

OTHER PUBLICATIONS

Coessens. J. Controlled Release. 1996, 38, pp. 141–150.*
Zignani. J Controlled Release. 1997, vol. 48, pp. 115–129.*
Hwang et al., Cationic ploymers for gene delivery: Designs for overcoming barriers to systemic administration, 2001, Molecular Therapautic, vol. 3, No. 2, pp. 1830–191.*
Mahato et al., Peptide–based gene delivery, 1998, Molecular Theapautic, vol. 1, No. 2, pp. 226–243.*
Heller et al., Release of Insulin from pH–Sensitive Poly–(Ortho Ester), 1990, Journal of Controlled Release, vol. 13, pp. 295–302.*
Richardson et al., Poly ( amidoamine)s as Potential Endosomloytic Polymers: Evaluation In Vitro and Body Distribution in Normal and Tumour–Bearing Animals, 1999, Journal of Targeting, vol. 6, No. 6, pp. 391–404.*
Rollan, Advance Gene Delivery, 1996, Control Rel, vol. 39, pp. 357–372.*
Hope et al., Cationic lipids, phosphatidlethanolamine and the intracellular delivery of polymeric, nucleic acid–based drugs (Review), 1998, Membrane Biology, vol. 15, pp. 1–14.*

Felgner et al. "Lipofection: A Highly Efficient, Lipid–Mediated DNA–Transfection Procedure" *Proc. Natl. Acad. Sci. USA* 84:7413–7417, 1987.
Goldman et al. "In vitro and in vivo gene delivery mediated by a synthetic polycationic amino polymer" *Nature Biotechnology* 15(5):462–466, 1997.
Gottschalk et al., "Synthetic Vehicles for Efficient Gene Transfer and Expression in Mammalian Cells (Meeting Abstract)", *J. Cell Biochem.*, (Suppl. 21A) 393, 1995.
Hagmann, et al., "Release of Endosomal Content Induced by Plasma Membrane Tension: Video Image Intensification Time Lapse Analysis", *Experimental Cell Research*, 198: 298–304, 1992.
Harris "Gene Delivery and Therapy Strategies" *The Lancet* 342:234, 1993.
Harris, et al., "Receptor–Mediated Gene Transfer to Airway Epithelial Cells in Primary Culture", *Am. J. Respir. Cell Mol. Biol.* 9(4): 441–447, 1993.
Hui, et al., "The Role of Helper Lipids in Cationic Liposome–Mediated Gene Transfer" *Biophys. J.* 71:590–599, 1996.
Kabonov et al., "DNA Complexes with Polycations for the Delivery of Genetic Material into Cells" *Bioconjugate Chemistry*, 6(1): 7–20, 1995.
Kornguth et al., "Effect of Polylystine on the Leakage and Retention of Compounds by Ehrlich Ascites Tumor Cells" *Cancer Research*, 21:907–912, 1961.
Kuo et al. "Novel systems for controlled delivery of macromolecules" *Critical Reviews Euk. Gene Exp.* 6(1):59–73, 1996.
Ledley "Pharmaceutical approach to somatic gene therapy" *Pharmaceutical Research* 13(11):1595–1614, 1996.

(List continued on next page.)

Primary Examiner—Dave T. Nguyen
(74) Attorney, Agent, or Firm—Brenda Herschbach Jarrell; C. Hunter Baker; Choate, Hall & Stewart

(57) ABSTRACT

The present invention provides improved cell delivery compositions. In particular, the invention provides biocompatible endosomolytic agents. In a preferred embodiment, the endosomolytic agents are also biodegradable and can be broken down within cells into components that the cells can either reuse of dispose of. In one aspect, the present invention provides endosomolytic agents capable of effecting the lysis of an endosome in response to a change in pH, and methods for effecting the lysis of an endosome. These inventive endosomolytic agents obviate the need for known agents (i.e., chloroquine, fusogenic peptides, inactivated adenoviruses and polyethyleneimine) that can burst endosomes and have negative effects on cells. In another aspect, the present invention provides cell delivery compositions comprising an endosomolytic component that is capable of effecting the lysis of the endosome in response to a change in pH, and an encapsulating, or packaging, component capable of packaging a therapeutic agent to be delivered to cellular or subcellular components.

34 Claims, 7 Drawing Sheets

OTHER PUBLICATIONS

Ledley "Nonviral gene therapy: The promise of genes as pharmaceutical products" *Human Gene Therapy* 6(9):1129–1144, 1995.

Liang, et al., Characterization of a pH–Sensitive Surfactant Biochimica ET Biophysica Acta, 1369(1): 39–50.

Midoux et al. "Efficient Gene Transfer by Histidylated Polylysine/pDNA Complexes" *Bioconjugate Chemistry* 10(3):406–411, 1999.

Miller et al. "Studies of the Mechanistic Diversity of Sodium Cyanoborohydride Reduction of Tosylhydrazones", *J. Org. Chem.* 54:4175–4188, 1989.

Plank et al. "The Influence of Endosome–Disruptive Peptides on Gene TransferUsing Synthetic Virus–Like Gene Transfer Systems", *J. Biol. Chem.* 269(17):12918–12924, 1994.

Schwarzenberger et al., "Receptor–Targeted Recombinant Adenovirus Conglomerates: A Novel Molecular Conjugage Vector with Improved Expression Characteristics" *J. Virol.* 71(11): 8563–8571, 1997.

Seglen "Inhibitors of lysosomal function" *Methods Enzymol.* 96:737–764, 1983.

Suh et al. "Ionization of Poly(ethylenimine) and Poly(allylamine) at Various pH's", *ioorg. Chem.* 22:318–327, 1994.

Tomlinson et al. "Controllable gene therapy pharmaceutics of non–viral gene delivery systems" *J. Controlled Release* 39(2–3):357–372, 1996.

Wagner, et al., "Transferrin–Polycation Conjugates as Carriers for DNA Uptake Into Cells" *Proc. Nat. Acad. Sci. USA.*, 873410–3414, 1990.

Wagner, et al., "Influenza Virus Hemagglutinin HA–2N–Terminal Fusogenic Peptides Augment Gene Transfer by Transferrin–Polylysine–DNA Complexes: Toward a Synthetic Virus–Like Gene–Transfer Vehicle" *Proc. Natl. Acad. Sci. USA*, 89:7934–7938, 1992.

Wagner, "Receptor–Mediated Gene Transfer: The Answer in Tumor Immunotherapy?" *Molekularbiol. Grundlagen Gastroenterol.*, (Beger et al., eds.) Berlin: Springer–Verlag, 389–392, 1995.

Wagner, et al., "Receptor–Mediated Delivery of Plasmid DNA" *Biogenic Amines*, 14(5): 519–536, 1998.

Wu et al., "Incorporation of Adenovirus into a Ligand–Based DNA Carrier System Results in Retention of Original Receptor Specificity and Enhances Targeted Gene Expression", *J. Biol. Chem.* 269:11542, 1994.

Wu et al., "Receptor–Mediated Gene Delivery and Expression in Vivo" *Biol. Chem.* 263:14621, 1998.

Zatloukal et al., "Tranferrinfection: A Highly Efficient Way to Express Gene Constructs in Eukaryotic Cells" *Ann. N.Y. Acad. Sci.* 660136–153, 1992.

Zauner, et al., "Glycerol and Polylysine Synergize in their Ability to Rupture Vesicular Membranes: A Mechanism for Increased Transferrin–Polylysine–Medicated Gene Transfer" *Exp Cell Res.*, 232: 137–145, 1997.

Zauner, et al., "Polylysine–Based Transfection Systems Utilizing Receptor–Mediated Delivery" *Adv. Drug Delivery Res.*, 30: 97–113, 1998.

Zauner et al. "Glycerol Enhancement of Ligand–Polylysine/DNA Transfection" *Biotechniques* 20:905–913, 1996.

Zenke, et al., "Receptor–Mediated Endocytosis of Transferrin–Polycation Conjugates: An Efficient Way to Introduce DNA into Hematopoietic Cells" *Proc. Natl. Acad. Sci. USA*, 87: 3655–3659, 1990.

\* cited by examiner

FIG. 1
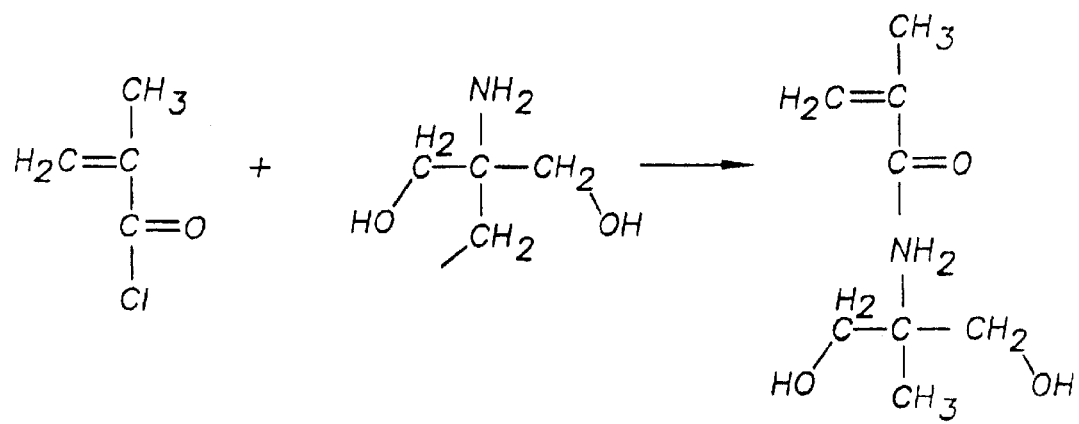
(1)
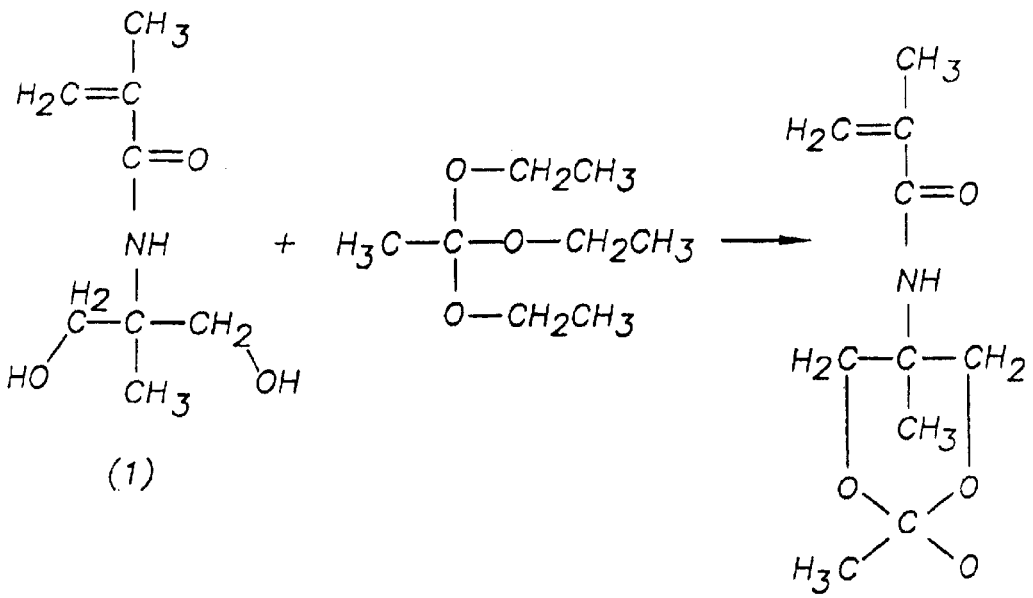
(1)
(2)

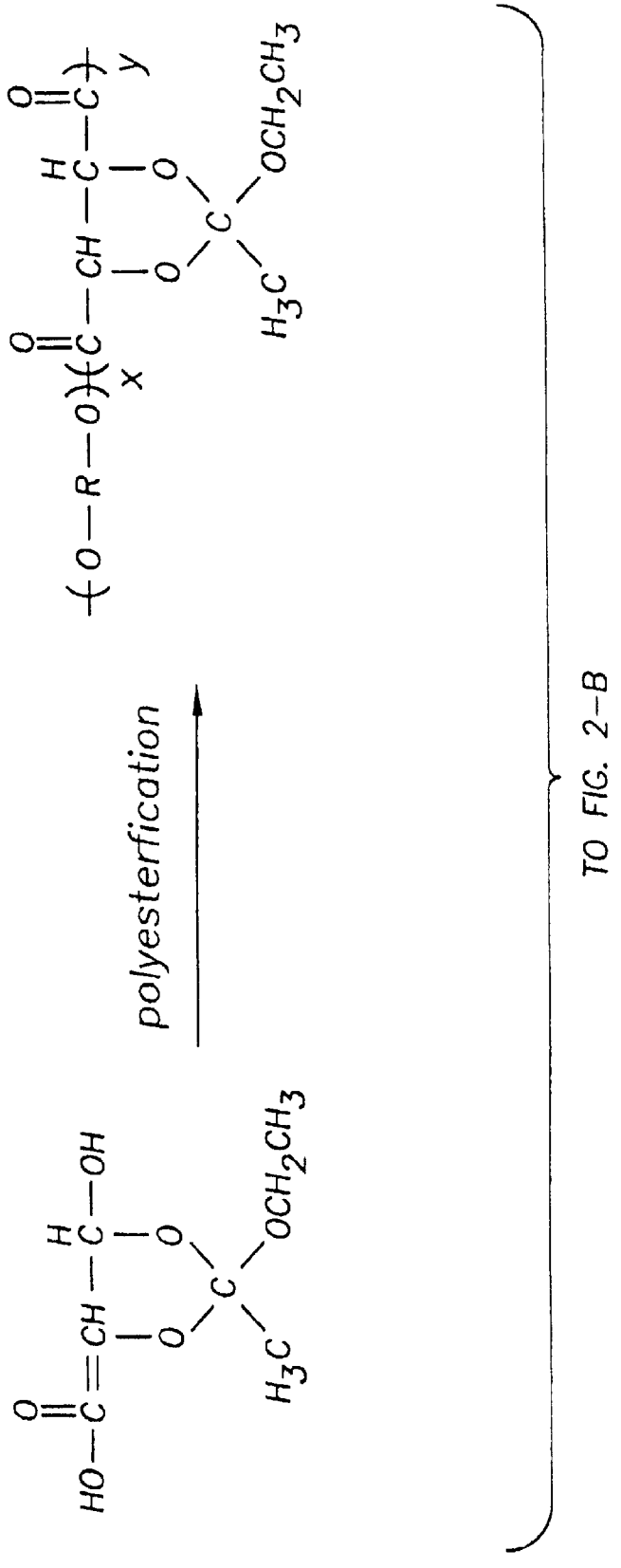
FIG.2-A

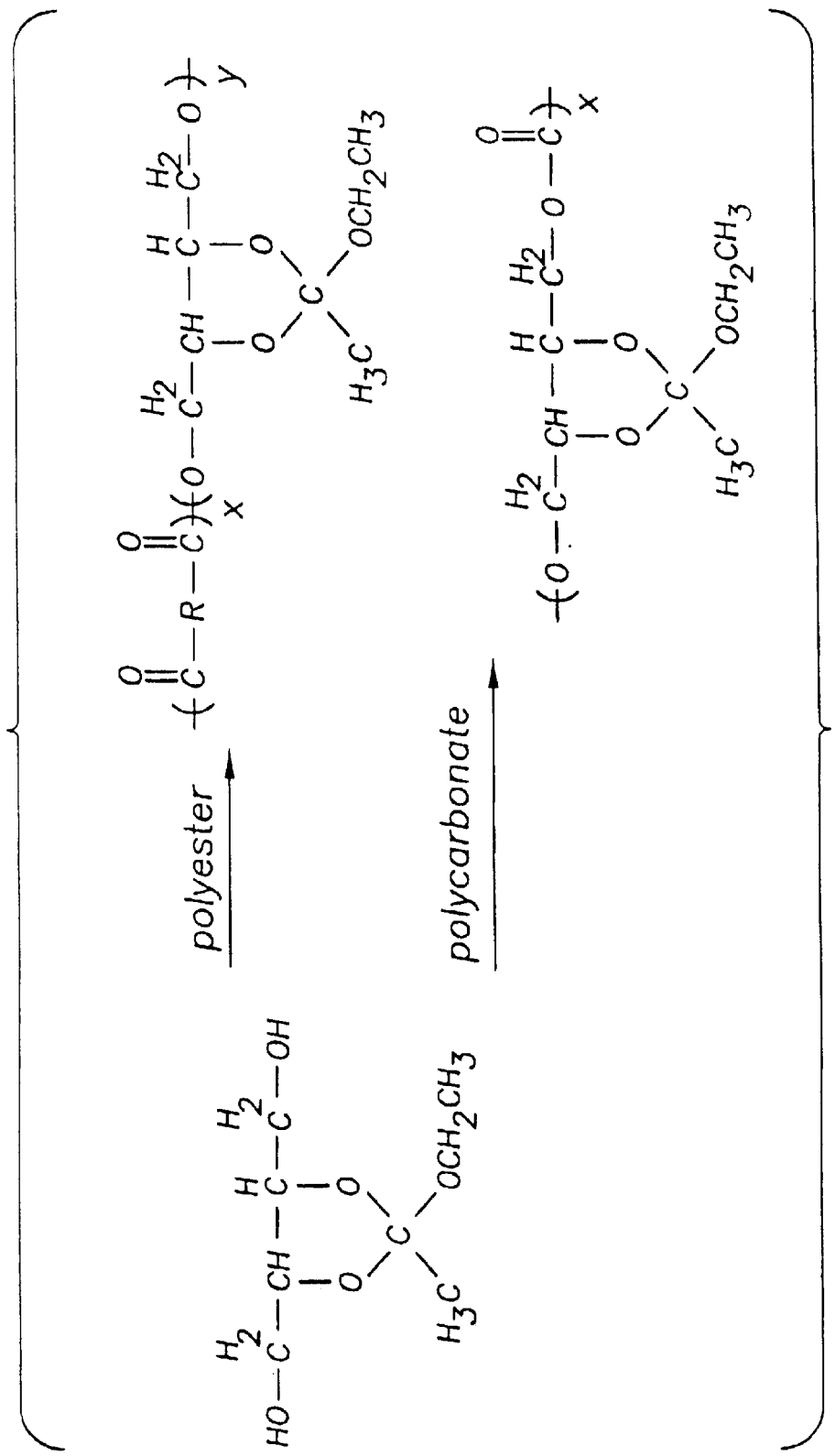
FIG. 2-B

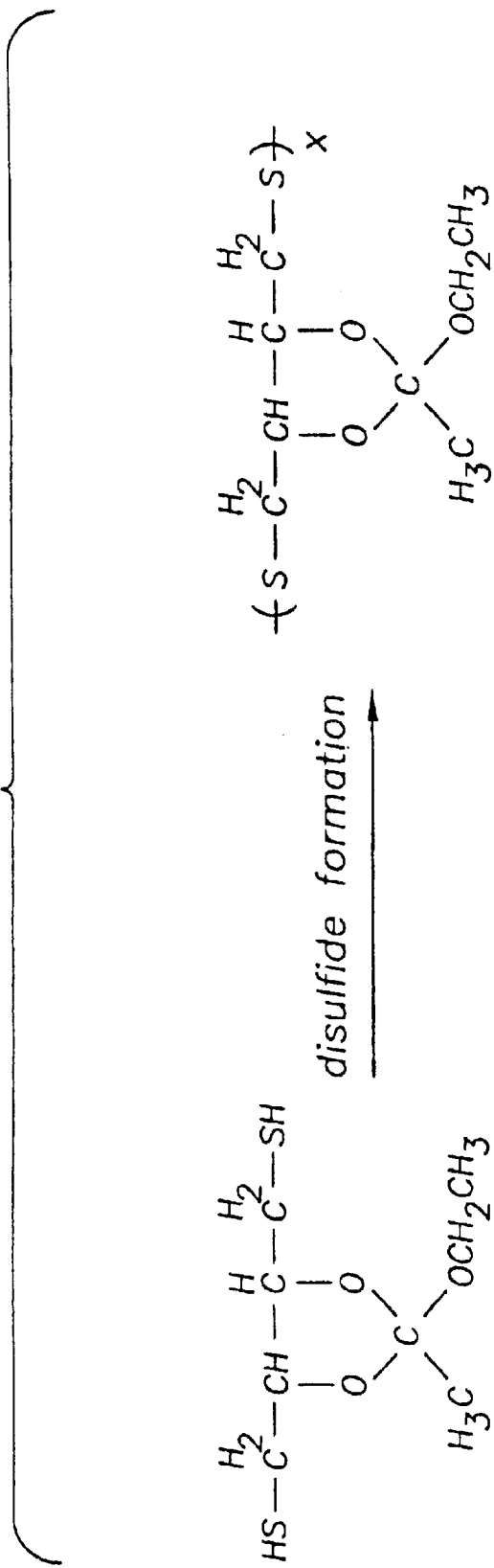
FIG. 2-C

FIG. 3
(3-aminopropyl)methacrylamide/polyvinyls
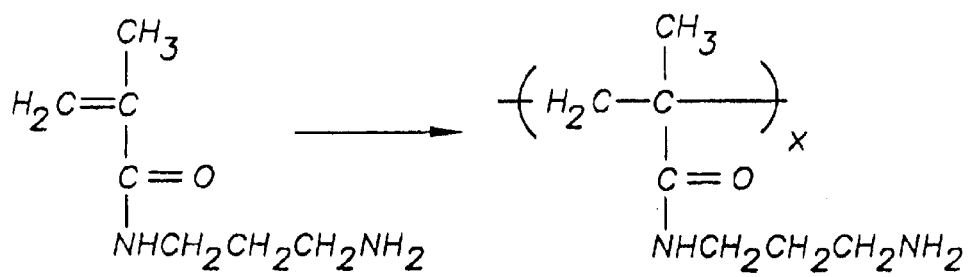
(2-aminoethyl)methacrylamide/polyvinyls
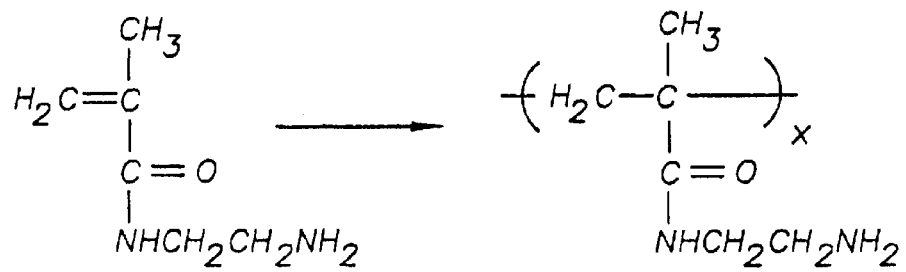
Aspartic acid or glutamic acid/polyesters
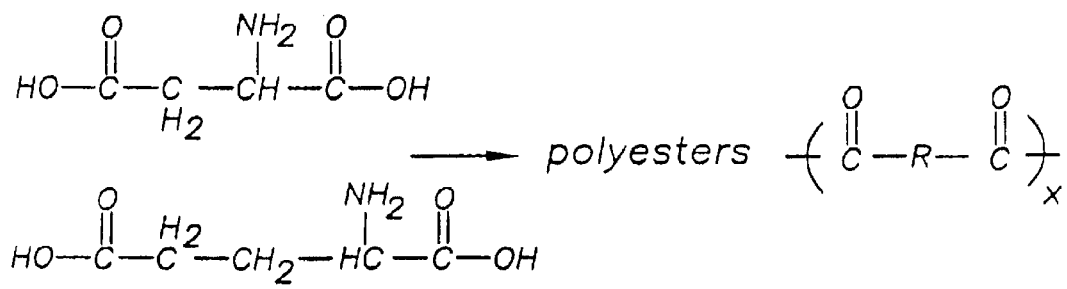

| Percent | Lower | Upper |
|---|---|---|
| By Inten. | 100 | 0 |
| By Weight | 100 | 0 |
| By Number | 100 | 0 |

Mean = 97 nm
Var. = 0.818
Skew = 0.234
RMS = 1.59E-83

ENDOSOMOLYTIC AGENTS AND CELL DELIVERY SYSTEMS

PRIORITY APPLICATIONS

The present application claims priority to provisional application 60/130,362, entitled "Endosomolytic Agents and Cell Delivery Systems", filed Apr. 21, 1999, the entire contents of which are incorporated herein by reference.

BACKGROUND OF THE INVENTION

The recent advances in drug discovery and molecular and pharmaceutical biology have created a need for the development of effective mechanisms for delivering therapeutic agents into cells. In but one example, researchers have particularly struggled to develop efficient means for introducing nucleic acids into cells. The development of a method to efficiently introduce nucleic acids into cells would be useful, for example, in gene therapy, antisense therapy, research purposes (e.g., to study cell differentiation, growth and carcinogenic transformation or for the creation of animal models for human disease; see, for example, Abdallah, Biol. Cell, 1995, 85, 1, and references therein).

An efficient way in which nature has accomplished the task of delivering biological agents into cells is through the evolution of viruses specifically to mediate the transfer of genetic materials into cells. Although viruses are ideal vectors for gene therapy because they have the highest levels of transfection efficiency known, the human immune system has likewise evolved to counteract viral infections, thus making virus-based gene therapy in humans potentially unsafe. Because of this characteristic of viral gene delivery systems, non-viral, or synthetic, gene delivery systems have been created to mediate the transfer of therapeutic agents into cells. Unfortunately, existing techniques for delivering nucleic acids to cells are limited by poor efficiency and/or high toxicity of the delivery reagents. A particular problem is encountered with techniques that rely on receptor-mediated endocytosis because the nucleic acid to be delivered is often destroyed when exposed to the low pH and active degradatory machinery of the endosome/lysosome. Various reagents (e.g., chloroquine, polyethyleneimine [PEI], certain highly charged cationic compounds, fusogenic peptides, and inactivated adenoviruses) have been developed that are intended to quickly disrupt the endosome in order to minimize the amount of time that a delivered nucleic acid spends in this hostile environment. Specifically, two delivery systems that have obtained recognition as the forerunners for in vivo gene therapy are those based on polymers and on lipids.

The first polymer used for a gene delivery system was polylysine (Wu, G. Y., Wu, C. H. J Biol. Chem. 1988, 263, 14621), in which the polylysine was complexed with plasmid DNA and evaluated for its ability to mediate the transfection of cells. Polylysine continues to be a common choice for the study of gene transfer, however, the gene expression mediated by polylysine, and other like polycations, is low. In an effort to increase the transfection efficiency of polylysine and other like polycations, agents designed to destabilize the endosome have been typically used in conjunction with lysine. One example of such an agent is chloroquine, which is a weak base that buffers the endosome to maintain a neutral endosomal pH. This buffering effect serves two functions to increase transfection efficiency (Seglen, P. O. "Inhibitors of lysosomal function" Methods Enzymol. 1983, 96, 737). First, the enzymes of the lysosome (which fuses with the endosome to form a secondary lysosome) have maximum activity in an acidic medium. Therefore, buffering of the vesicle diminishes the activity of the enzymes including nucleases that can degrade the therapeutic plasmid DNA. Second, the buffering effect may also act to cause vesicle expansion and subsequent destabilization of the endosome. While chloroquine provides an effective system to study the transfection efficiencies of delivery systems in vitro, its use in vivo is unrealistic owing to the high local concentrations required to increase the gene expression. One substitute utilized for chloroquine includes glycerol, which has recently been shown to enhance gene expression in vitro. However, 1–1.5 M glycerol is required to enhance transfection, thus also making glycerol impractical for in vivo gene transfer Zauner, W.; Kichler, A., Schmidt. W.; Sinski, A.; Wagner, E. Biotechniques 1996, 20, 905). Other approaches used to increase the gene expression by polylysine/DNA conjugates rely on virus or virus components. For example, the addition of adenovirus to a polylysine/DNA complex increased transfection levels over 2000 times in vitro (Wu, G. Y.; Zhan, P.; Sze, L. L.; Rosenberg, A. R.; Wu, C. H. J. Biol. Chem. 1994, 269, 11542), and conjugation of endosomolytic peptides to polylysine/DNA complexes increased transfection efficiency more than 1000 times in vitro (Plank, C.; Oberhauser, B.; Mechtler, K.; Koch, C.; Wagner, E. J. Biol. Chem. 1994, 269, 12918). However, the inclusion of potentially immunogenic protein-based endosomolytic agents into gene delivery systems may significantly diminish the utility of the conjugate for repeated use in vivo.

Another synthetic polymer that has been recently evaluated for its ability to mediate gene transfer is polyethyleneimine (PEI) which contains primary, secondary, and tertiary amines (Abdallah, B.; Hassan, A.; Benoist; Goula, D.; Behr, J. P.; Demeneix, B. A. Human Gene Therapy 1996, 7, 1947; Boussif, O.; Lezoualc'h, F.; Zanta, M. A.; Mergny, M. D., Scherman, D.; Demeneix, B.; Behr, J. P. Proc. Natl. Acad. Sci. USA 1995, 92, 7297). The advantage of PEI over polylysine as a mediator for gene transfer is that it contains a built-in mechanism for endosome escape. The overall protonation of PEI at pH=7 is approximately 20% whereas the overall protonation at pH=5 is approximately 45% (Suh, J.; Paik, H. J.; Hwang, B. K. Bioorg. Chem. 1994, 22, 318). These different protonation levels suggest that PEI is capable of buffering the endosome in the same manner as chloroquine. In fact, PEI is capable of mediating gene transfer equal to the best lipid systems. However, while PEI demonstrates that the synthetic "built-in" mechanism for endosomal rupture works well to mediate gene transfer, PEI is toxic to cells in vitro (Personal experimental evaluation, MIT, April 1998).

In addition to synthetic polymers, lipids have also been extensively studied for uses in gene therapy. These lipids are generally cationic lipids containing a positively charged head group and a hydrophobic tail. The first widely recognized lipid-based DNA delivery system was a mixture of DOTMA (N-1,2,3-dioleyloxy)propyl]-N,N, N-trimethylammonium chloride) and DOPE (dioleoyloxy phosphatidylethanolamine) known as Lipofectin (Felgner, P. L.; Gadek, T. R.; Holm, M.; Roman, R.; Chan, H. W.; Wenz, M.; Norhrop, J. P.; Ringold, G. M.; Daneilsen, M. Proc. Natl. Acad. Sci. USA, 1987, 84, 7413). Since Lipofectin was introduced many lipid-based gene transfer systems were synthesized, such as DOGS (dioctadecylamidoglycylspermine), DDAB (dimethyldioctadecylammonium bromide) and DOTAP ([1, 2-dioleoyl-3-trimethylammonium-propane). Although lipid-based systems generally have transfection efficiencies superior to polymer-based systems, their levels of transfection are still generally insufficient for practical clinical somatic gene therapy.

Although attempts have been made to improve each of these known endosomolytic agents, they still possess toxicity problems and other disadvantages. Clearly, a versatile and biocompatible synthetic cell delivery system, preferably biodegradable, would be important for the clinical success of gene delivery and the delivery of other therapeutic agents.

SUMMARY OF THE INVENTION

The present invention provides improved cell delivery systems. In particular, the invention provides a novel endosomolytic agent capable of effecting the lysis of an endosome in response to a change in pH. The inventive endosomolytic agents obviate the need for known agents (i.e., chloroquine, fusogenic peptides, inactivated adenoviruses and polyethyleneimine) that can burst endosomes but that have negative effects on cells. In certain preferred embodiments, this endosomolytic agent comprises a compound having at least one hydrolyzable functional moiety, and wherein said compound is capable of undergoing a hydrophobic/hydrophilic transition and effecting lysis of the endosome in response to a change in pH. In a particularly preferred embodiment, this functional moiety comprises an ortho-ester. In certain other embodiments, the endosomolytic agent comprises a compound having synergistic components. In a particularly preferred embodiment, this synergistic agent comprises a compound having at least one hydrolyzable functional moiety, and at least one other functional moiety capable of undergoing an ionization event, wherein the compound is capable of undergoing a hydrophobic/hydrophilic transition and effecting lysis of the endosome in response to a change in pH.

In another aspect, the invention also provides a cell delivery system comprising the endosomolytic agent or component as described above, and additionally a packaging component. In one embodiment, the cell delivery system is formulated as a polymer, wherein monomers comprising encapsulating components and endosomolytic components, are polymerized as a single linear or a branched polymer. In another embodiment, the cell delivery system is formulated as a mixture of endosomolytic and encapsulating components, but are not copolymerized. Whether copolymerized or formulated as a mixture, any appropriate combination of components may be utilized that results in delivery of a desired agent to the cell or subcellular component. Particularly preferred agents to be delivered include, but are not limited to therapeutic agents such as nucleic acids, biomolecules and small molecules, however one of ordinary skill in the art will realize that other agents to be delivered to cells, including, but not limited to contrast agents, could be utilized in the present invention.

As one of ordinary skill in the art will realize, the endosomolytic agents and the cell delivery agents of the present invention must be of appropriate size to fit inside an endosomal compartment, along with any agent to be delivered to the cell. Inventive agents and compositions are therefore preferably less than about 150 nm in size, or are capable of adopting a conformation less than about 150 nm in size for purposes of uptake via endocytosis.

Additionally, in particularly preferred embodiments, the endosomolytic agents and the cell delivery compositions are biocompatible and biodegradable.

Definitions

"Biocompatible": The term "biocompatible", as used herein, is intended to describe compounds that are not toxic to cells. Compounds are "biocompatible" if their addition to cells in vitro results in less than or equal to 20% cell death and do not induce inflammation or other such adverse effects in vivo.

"Biomolecules": The term "biomolecules", as used herein, refers to molecules (e.g., proteins, amino acids, nucleic acids, nucleotides, carbohydrates, sugars, lipids, etc.) that are found in living cells in nature.

"Small molecule": The term "small molecule", as used herein, refers to organic molecules either synthesized or found in nature, generally having a molecular weight less than 1000, however the definition of small molecule is not limited by this number.

"Biodegradable": As used herein, "biodegradable" compounds are those that, when introduced into cells, are broken down by the cellular machinery into components that the cells can either reuse or dispose of without significant toxic effects on the cells (i.e., fewer than about 20% of the cells are killed)

DESCRIPTION OF THE DRAWING

FIG. 1 depicts the synthesis of the monomer N-[2-methyl-1,3-O-ethoxyethylidine-propanediol]methacrylamide.

FIG. 2 depicts the use of ortho-ester protected tartaric acid, threitol, and dithiothreitol monomers.

FIG. 3 depicts particularly preferred cationic monomers for use in the present invention.

DESCRIPTION OF CERTAIN PREFERRED EMBODIMENTS

Figure 4:
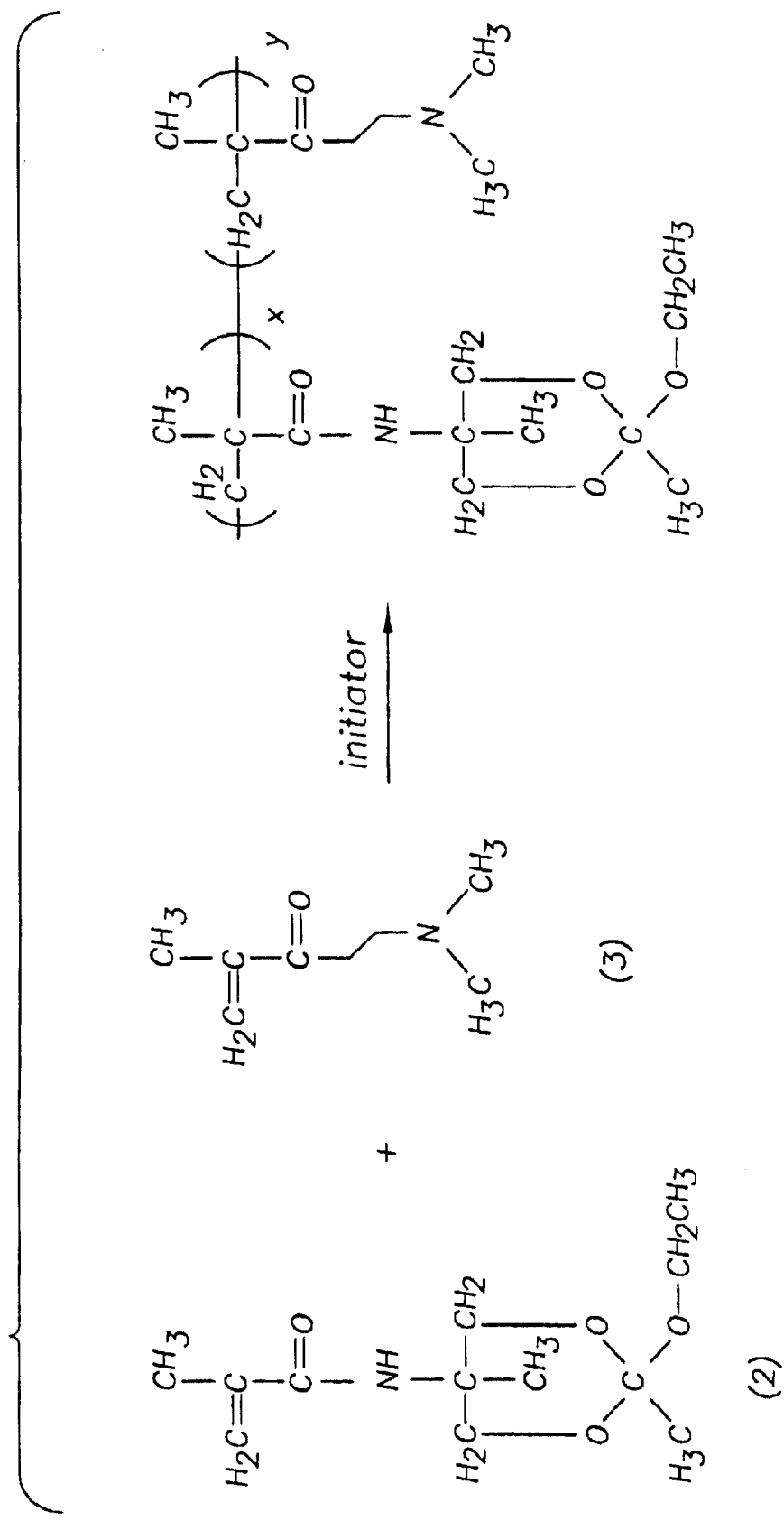
FIG. 4 depicts an example of copolymerization of monomers having encapsulating/packaging characteristics and monomers having endosomolytic characteristics.

In recognition of the importance of the development of a safe and effective cell delivery system, the present invention provides improved compositions and methods for the delivery of therapeutic agents to cells and subcellular components. In one aspect, the present invention provides an endosomolytic system that is capable of effecting the lysis of an endosome in response to a change in pH, and methods for effecting the lysis of an endosome. These inventive endosomolytic agents obviate the need for known agents (i.e., chloroquine, fusogenic peptides, inactivated adenoviruses and polyethyleneimine) that can burst endosomes and have negative effects on cells. In another aspect, the present invention provides cell delivery compositions comprising an endosomolytic component that is capable of effecting the lysis of the endosome in response to a change in pH, and an encapsulating component capable of packaging a therapeutic agent to be delivered to cellular or subcellular components. In particularly preferred embodiments, the endosomolytic systems are biodegradable and/or bioresorbable.

Certain examples of preferred embodiments of endosomolytic systems and cell delivery systems will be described below.

Endosomolytic Agents

As discussed above, the present invention provides improved agents and systems for the delivery of compounds to cells and the lysis of endosomal cell compartments. These improved agents and systems are capable of lysing an endosome and/or releasing an agent from an endosome in response to a change in pH. In particular, the invention provides biocompatible, preferably biodegradable, endosomolytic agents. As one of ordinary skill in the art will realize, the endosomolytic agents of the present invention must be of appropriate size to fit inside an endosomal compartment, along with any agent to be delivered to the cell. Inventive agents are therefore less than about 150 nm in size, or are capable of adopting a conformation less than about 150 mm in size for purposes of uptake via endocytosis.

While the mechanism of action of the endosomolytic system is not intended to limit the scope of the present invention, preferred agents comprise compounds having one or more functional moieties that are capable, in response to a change in pH, of undergoing a hydrophobic/hydrophilic transition and releasing an agent known to disrupt lipid bilayers. In certain preferred embodiments, the hydrophobic/hydrophilic transition is initiated by the hydrolysis of specific functional moieties in the endosomolytic agent. This hydrolysis additionally results in the release of an agent capable of disrupting lipid bilayers thus lysing an endosome. A particularly preferred biocompatible agent capable of disrupting lipid bilayers includes, but is not limited to, ethanol.

In certain other embodiments, the endosomolytic agent comprises a compound having components capable of acting in a synergistic manner. In a particularly preferred embodiment, this synergistic agent comprises a compound having at least one hydrolyzable functional moiety, and at least one other functional moiety capable of undergoing an ionization event, wherein the compound is capable of undergoing a hydrophobic/hydrophilic transition and effecting lysis of the endosome in response to a change in pH.

Although in principle any compound having any combination of the above-described characteristics can be utilized, particularly preferred endosomolytic agents are polymers comprised of one or more monomers having one or more functionalities capable of effecting the hydrophobic/hydrophilic transition and/or release of an endosomolytic agent. In preferred embodiments, these polymers are prepared from monomers having one or more hydrolyzable functional moieties. In other preferred embodiments, these polymers are prepared from any combination of monomers having one or more hydrolyzable functional moieties and monomers having functional moieties capable of undergoing an ionization event.

In but one example, a preferred hydrolyzable moiety present in the inventive endosomolytic agent comprises an ortho-ester functionality. At pH=7, the ortho-ester is stable upon formation of the nanoparticles, however, at pH<5, which is encountered in the endosomal compartment, the ortho-ester functionality hydrolyzes, releases the endosomolytic compound ethanol, and thus is transformed into a hydrophilic diol functionality which is capable of effecting escape from the endosomal compartment into the cytoplasm. As one of ordinary skill in the art will realize, an endosomolytic agent can be prepared from monomers having ortho-ester functionalities, which are then subsequently polymerized.

In but one example, as shown in FIG. 1, the monomer N-[2-methyl-1,3-O-ethoxyethylidine-propanediol] methacrylamide (2) is synthesized from N-[2-methyl-1,3.20 propanediol]methacrylamide (1). This compound (1) can be readily synthesized by acylation of an amino diol with methacryloyl chloride according to literature procedure (Jedlinski, Z.; Paprotny, J. *Roczniki Chemii* 1986, 40, 1487) in which 2-amino-2-methyl-1,3-propanediol was reacted with methacryloyl chloride at −10° C. in acetonitrile for 24 hours. This compound contains two primary alcohols in a 1,3 configuration making it ideal for diol protection via an ortho-ester, as shown below in FIG. 1. Subsequent reaction, (according to literature procedure Miller, V.; Yang, D.; Weigel, T.; OHan, O.; Liu, H. *J. Org. Chem.* 1989, 54, 4175) with triethylorthoacetate in the presence of a catalytic amount of p-toluene sulfonic acid and recrystallization from acetone yields (2), which can then subsequently be polymerized to yield an inventive endosomolytic agent.

Other particularly preferred monomers for use in the preparation of inventive endosomolytic agents include, but are not limited to tartaric acid protected by ortho-ester formation, threitol protected by orthoester formation, and dithiothreitol protected by ortho-ester formation. Each of these can subsequently be polymerized to yield polyesters, polycarbonates, and polydisulfides, respectively, for use as endosomolytic agents, as also shown in FIG. 2.

Although FIG. 2 depicts the use of ortho-ester protected tartaric acid, threitol, and dithiotheitol monomers, one of ordinary skill in the art will realize that other monomers having functionalities capable of being protected using an ortho-ester functionality can be utilized. Additionally, one of ordinary skill in the art will also realize that the present invention is not limited to the use of ortho-ester functionalities; rather other functionalities capable of undergoing a transformation in response to a change in pH (generally from pH=7 to pH<5) upon endocytosis, and releasing an endosomolytic compound, can be utilized, including, but not limited to functionalities such as hydrazones and cis-actonyls. Moreover, it will also be realized that the preparation of inventive endosomolytic agents is not limited to the use of like monomers, such as those having only ortho-ester functionalities; rather, any combination of functionalities, for example, ortho-esters, hydrazones, and cis-actonyls, to name a few, may be utilized to prepare the inventive endosomolytic agents. These monomers may be associated with one another covalently (e.g., as a result of free radical polymerization) or otherwise, so long as the resulting endosomolytic agents are capable of lysing an endosome and are preferably also biocompatible.

As a variation of the use of a combination of a collection of monomers as described above, in another preferred embodiment, the endosomolytic agent is formulated from a combination of two or more monomers that exhibit a synergistic effect resulting in the lysis of the endosomal compartment. The endosomolytic agent comprises at least one monomer having a hydrolyzable moiety, including, but not limited to the ortho-ester functionality discussed above, and at least one other monomer having one or more functional moieties capable of undergoing an ionization event.

In but one example, an inventive synergistic system is prepared by combining a monomer having an ortho-ester functionality, which forms a hydrophilic diol following hydrolysis, with a ionizable comonomer such as N-methacryloyl-L-histidine that is capable of being protonated and increases the hydrophilicity of the polymer at pH=5, thus allowing the escape of the therapeutic agent to be delivered from the hydrophobic polymer matrix into the cytoplasm.

As one of ordinary skill in the art will realize, as discussed above, the inventive endosomolytic agents may be prepared from any combination of monomers having functionalities such as ortho-esters, hydrazones and cis-actonyls capable of release of an endosomolytic compound, and monomers capable of undergoing an ionization event, to provide inventive endosomolytic agents that function via a synergistic effect. These monomers may be associated with one another covalently (e.g., via free radical polymerization) or otherwise so long as the resulting endosomolytic agents are capable of lysing an endosome and are preferably also biocompatible.

Cell Delivery Systems

It is particularly preferred that the inventive endosomolytic agents are also utilized in combination with an encapsulating/delivery agent to provide an inventive cell delivery system. In one preferred embodiment, the endosomolytic agent or component and the encapsulating component comprise monomers that are copolymerized to provide an inventive cell delivery system. In another preferred embodiment, the endosomolytic component and the encapsulating component are not copolymerized, but are rather provided as a mixture to yield the inventive cell delivery system. The selection of the encapsulating component for use in accordance with the cell delivery system of the present invention, of course, depends on the compound to be delivered. The encapsulating component is any entity, preferably biocompatible and biodegradable, that interacts with the compound to be delivered in such a way as to mediate its introduction into a cell.

In one particularly preferred embodiment, the therapeutic agent to be delivered to the cell is DNA, and thus preferred encapsulating/packaging agents include compounds with a high charge density such as cationic polymers, particularly those synthesized from tertiary amines and quaternary amines. In but one example, the monomer 2-[dimethylamino]ethyl methacrylate can be utilized. Other particularly preferred cationic monomers include, but are not limited to (3-aminopropyl)methacrylamide, 2-aminoethyl methacrylamide, aspartic acid and glutamic acid, as shown in FIG. 3.

Although tertiary amines are more particularly preferred, quaternary amines such as trimethylammonioethyl methacrylate chloride can be utilized. As one of ordinary skill in the art, the cell delivery composition can also be synthesized using a combination of encapsulating components, similarly to utilizing a combination of endosomolytic components having a synergistic effect, to achieve encapsulation/packaging of a therapeutic agent.

As discussed previously, the individual monomers having encapsulating characteristics and endosomolytic characteristics are polymerized using standard reactions including, but not limited to free radical polymerizations. In but one example, for free radical polymerizations, initiator type, monomer/initiator ratio, polymerization temperature, polymerization time, polymerization solvent and comonomer ratio is varied. These parameters are known to influence the final properties of the polymer. FIG. 4 depicts one example of the copolymerization of monomers having encapsulating characteristics and endosomolytic characteristics via free radical polymerization. Those of ordinary skill in the art will, using known techniques, be able to prepare any of a variety of cell delivery compositions that can readily be tested according to the teachings herein to identify those with desirable delivery characteristics. These compositions preferably have sufficient endosomolytic character to lyse endosomes, and sufficient encapsulation character to package therapeutic agents.

As one of ordinary skill in the art will realize, the resulting collection of polymers can rigorously be characterized using several established methods such as determining monomer molar ratios and structural determination using $^1$H and $^{13}$C NMR spectroscopy, in which characteristic peaks can determined using homopolymers of each monomer and the ratio of these peaks can be used to quantify the ratios of the monomers in each polymer synthesized. Other characterization techniques familiar to one of ordinary skill in the art include, but are not limited to elemental analysis, multi-detector (laser light scattering, differential viscometry, and differential refractometry) and gel permeation chromatography (GPC).

Once the polymers have been characterized, the encapsulation capability of the inventive system is tested. In but one example, DNA-containing nanoparticles are formulated for the pH sensitive polymers using a variety of methods, including, but not limited to spontaneous emulsification, sonication, or homogenization, and are evaluated for particle size formation. Spontaneous emulsification is a particularly preferred method because this method has been reported to effectively encapsulate hydrophilic compounds in hydrophobic polymer matrices without resulting DNA damage.

In but one example, the ability of DNA to escape from the cell delivery composition, is evaluated using labeled polymers in cultured cells including, but not limited to, COS-7 (monkey fibroblast), HepG2 (human hepatoblastoma) and P388D1 (mouse macrophage), which can then be subsequently evaluated using confocal microscopy.

As discussed previously, the biocompatibility of the inventive system is particularly preferred. Biocompatiblity is if a primary concern for a proposed polymer-based gene delivery system. Although escape from the endosome is necessary for high transfection efficiency, biocompatibility of the delivery system is also required because a delivery system that is incompatible with a cell on the molecular level is apt to disrupt the normal cellular biochemistry, likely resulting in a low overall transfection efficiency. For gene therapy, biocomptability is a function of efficacy. Using cell lines, including, but not limited to, COS-7, HepG2, and P388D1, the biocompatibility of the abovementioned compounds can be determined as a function of the increasing concentration of these compounds to evaluate the safety of the inventive system. Although the abovementioned example (discussed further in Examples 4 and 5) focuses on the delivery of nucleic acids, one of ordinary skill in the art will realize that standard techniques in the art can be utilized to evaluate the ability of other therapeutic agents such as polysaccharides or small molecule drugs, to name a few, to be delivered to cells.

Targeting Agents

Furthermore, as one of ordinary skill in the art will realize, it is often desirable to target an agent to be delivered to a particular cell or collection of cells. A variety of agents that direct compositions to particular cells are known in the art (see, for example, Cotten et al., *Methods Enzym*, 217:618, 1993). Preferred targeting agents are biocompounds, or portions thereof, that interact specifically with individual cells, small groups of cells, or large categories of cells. Examples of useful targeting agents include, but are in no way limited to, low-density lipoproteins (LDLs), transferrin, asiaglycoproteins, gp120 envelope protein of the human immunodeficiency virus (HIV), and diptheria toxin, antibodies, and carbohydrates.

Certain preferred endosomolytic and cell delivery compositions of the present invention include one or more targeting agents associated with (e.g., by covalent, hydrophobic, hydrogen-bonding, van der Waals, or other interaction) the inventive endosomolytic agent, the encapsulation/delivery agent, and/or the delivery compound.

Delivery Compounds

As discussed previously, in principle, any substance having biological activity or therapeutic utility may be delivered to cells using the endosomolytic and/or cell delivery systems of the present invention. For example, the invention includes but is not limited to delivery of proteins, polypeptides, polynucleotides, nucleoproteins, polysaccharides, glycoproteins, lipoproteins, and synthetic and biologically engineered analogs thereof.

Examples of biologically active compounds that might be utilized in a delivery application of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. §§ 330.5, 331 through 361; 440–460; drugs for veterinary use listed by the FDA under 21 C.F.R. §§ 500–582, incorporated herein by reference, are all considered acceptable for use in the present inventive cell delivery composition.

Biologically active compounds for use in the present invention include any pharmacologically active substances that produce a local or systemic effect in animals, preferably mammals, or humans. The term thus means any substance intended for use in the diagnosis, cure, mitigation, treatment or prevention of disease or in the enhancement of desirable physical or mental development and conditions in an animal or human.

Classes of pharmaceutically active compounds that can be used in the practice of the present invention include, but are not limited to, anti-AIDS substances, anti-cancer substances, antibiotics, immunosuppressants (e.g., cyclosporine), anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, vaccines, ribozymes, anti-sense agents, and RNA.

A more complete listing of classes of compounds suitable for delivery into cells according to the present invention may be found in the Pharmazeutische Wirkstoffe (Von Kleemann et al. (eds) Stuttgart/N.Y., 1987, incorporated herein by reference). Examples of particular pharmaceutically active substances are presented below:

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine (acyclovir), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromicin and cephalosporins.

Anti-viral agents are substances capable of destroying or suppressing the replication of viruses. Examples of anti-viral agents include a-methyl-P-adamantane methylamine, 1,-D-ribofuranosyl-1,2,4-triazole-3 carboxamide, 9-[2-hydroxy-ethoxy]methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine,1-hydroxy maleate, iodotubercidin, p-bromotetramisole, 10-(alpha-diethylaminopropionyl)-phenothiazine hydrochloride, calmidazolium chloride, hemicholinium-3,3, 5-dinitrocatechol, diacylglycerol kinase inhibitor I, diacylglycerol kinase inhibitor II, 3-phenylpropargylamine, N6-monomethyl-L-arginine acetate, carbidopa, 3-hydroxybenzylhydrazine HCl, hydralazine HCl, clorgyline HCl, deprenyl HCl,L(-)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzyl amine (DCMB), 8,9-dichloro-2,3,4,5-tetrahydro-1H-2-benzazepine hydrochloride, p-aminoglutethimide, p-aminoglutethimide tartrate, R(+)-, p-aminoglutethimide tartrate, S(-)-, 3-iodotyrosine, alpha-methyltyrosine, L-, alpha-methyltyrosine, D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1, 2,3,6-tetrahydro-pyridine hydrochloride, 1-methyl-4-phenyl-2,3-dihydropyridinium perchlorate, N-methyl-4-phenyl-1,2,5,6 tetrahydropyridine HCl,1-methyl-4-phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, and the like.

Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenyloin, valproate, Chk and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timolol, timolol salts, and combinations of timolol, and/or its salts, with pilocarpine.

Anti-parasitic, -protozoal and -fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, pheneizine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

Uses

Those of ordinary skill in the art will immediately appreciate that the present invention can be utilized in a wide variety of applications to deliver agents into cells. A few particularly preferred applications are discussed in more detail here in order to highlight some of the characteristics and advantages of the inventive systems.

As discussed at length above, the present invention is particularly well adapted for delivery of nucleic acids into cells. As such, the inventive compositions are useful for various applications including gene therapy and antisense regulation. To give but a few examples of particular embodiments of nucleic acid delivery applications of the present invention, inventive compositions can be employed to introduce a gene into specific cells or tissue that will express the protein encoded by that gene and thereby correct a defect caused by a deficiency in that gene in the cells or tissue. Alternatively, inventive compositions can also be used to turn off the function of a specific gene, for example an oncogene in a tumor cell, by delivering anti-sense messenger RNA into a cell that will bind with the sense messenger RNA so that translation of the message and therefore expression of the protein encoded by that message will not occur.

Inventive compositions can be used in therapeutic gene delivery applications, for example to introduce "suicide genes" into cancer cells that will turn on the cell death pathway. Drug sensitivity genes can also be introduced into tumor cells. For example, cells can be genetically engineered to express prodrug activating enzyme, such as herpes simplex virus thymidine kinase, which phosphorylates ganciclovir creating toxic metabolites that kill tumor cells upon exposure to prodrug.

In the arena of immunotherapy, inventive compositions can be employed in "adoptive immunotherapy" preparations, in which genetically engineered tumor-infiltrating lymphocytes are prepared that express tumor necrosis factor and can be used to treat patients with melanoma. Immunomodulation of tumor cells to invoke an immune response directed toward specific target cell population is yet another area to which this invention can be applied.

Of course, as has already been emphasized, the inventive compositions are not limited in their usefulness to delivery of genes, or even nucleic acids; the compositions can alternatively be used to carry a variety of pharmaceutical compositions. (See Harris, *The Lancet*, 342:234, 1993).

EXAMPLES

Example 1

Synthesis of N-[2-methyl-1,3-propanediol] methacrylamide: The synthesis of this monomer precursor (1) was performed using a previously described method (Medlinski, Z. and Paprotny, J. *Roczniki Chemii* 1966, 40, 1487). The compound was obtained by acylating 2-amino-2-methyl-1,3-propanediol with methacryloyl chloride at −10° C. in acetonitrile for 24 hours. Following reaction, the product was isolated and purified by repeated recrystallization from acetonitrile to yield the product in 25% yield, melting point 101° C.–102° C. (lit. 102° C.–103° C.); Elemental Analysis Calc: C: 55.5%, H: 8.7%, N: 8.1%; Found: C: 55.2%, H: 8.7%, N: 8.0%

Example 2

Synthesis of N-[2-methyl-1,3-O-ethoxyethylidine-propanediol]methacrylamide: This monomer is synthesized by reaction of (1) with triethylorthoacetate using a previously reported method (Miller, V.; Yang, D.; Weigel, T.; OHan, O.; Liu, H.; *J. Org. Chem.* 1989, 54, 4175). Briefly, (1) suspended in dichloromethane is reacted for 24 h with triethylorthoacetate in the presence of a catalytic amount of p-toluenesulfonic acid. The solvent is then removed by rotoevaporation and the product is isolated and purified by repeated recrystallization from acetone.

Example 3

Polymer synthesis: Monomer (2) described above and 2-[dimethylamino]ethyl methacrylate (3) (purchased from Aldrich Chemical Company and purified by distillation) are polymerized by free radical polymerization under various conditions using a fractional factorial experimental design. In this method, the initiator type, monomer/initiator ratio, polymerization temperature, polymerization time, polymerization solvent, and comonomer ratio have been chosen as the variable parameters for polymerizations. These parameters are known to most greatly influence the final properties of the polymer (Billmeyer, F. W. Textbook of Polymer Science, John Wiley and Sons, 1984). Because it is essential that the polymers used for the structure activity relationship determinations have their exact chemical makeups known, the polymers resulting from the above series of experiments are rigorously conducted. The monomer molar ratios and structural determination of the polymers are conducted using $^1$H and $^{13}$C NMR spectroscopy. Characteristic peaks for each monomer are determined using homopolymers of each monomer and the ratio of these peaks are used to quantify the ratios of the monomers in each polymer synthesized. The elemental analysis for each polymer are also obtained and the results are correlated to the NMR spectra as a secondary evaluation of the monomer ratios. The molecular weight of each polymer is determined using multi-detector (laser light scattering, differential viscometry, and differential refractometry) gel permeation chromatography (GPC). From the GPC analysis the weight average molecular weight (Mw), number average molecular weight (Mn) and the polydispersity (Mw/Mn) are calculated. Also, from the GPC it is determined if any residual monomers are present in the final polymer. If residual monomer is found, the polymer will be continuously purified by precipitation until no residual monomer remains. No polymers that contain residual monomers will be used for DNA encapsulation experiments, endosomal escape experiments, or biocompatibility experiments. The glass transition (Tg) and melting (Tm) temperatures of the polymers are analyzed by differential scanning calorimetry (DSC). Also, any crystalline structures in the polymers are determined by DSC.

Example 4

Nanoparticle Formulation

Figure 5:
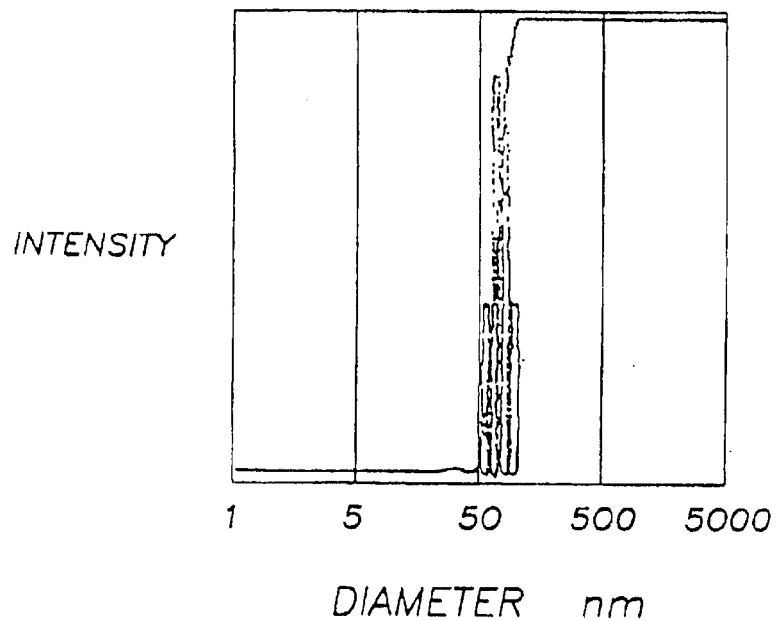
FIG. 5 depicts the size and polydispersity of DNA-containing PLGA Nanoparticles formulated by spontaneous emulsification.

The DNA-containing nanoparticles are formulated by spontaneous emulsification as described. FIG. 5 depicts an example of the nanoparticle formulation with DNA using spontaneous emulsification and shows the size and polydispersity. The polymer and plasmid DNA (marker plasmids pCMV-βGal or pCMV-luc) are dissolved in a cosolvent system consisting of acetone, water, and dichloromethane. The ratios of the solvents in the cosolvent system are varied with respect to: 1) each other, 2) the polymer amount, and 3) the plasmid DNA amount, to create a cosolvent system that creates nanoparticles with the desired properties. This solution is poured into a stirring cosolvent system that creates nanoparticles with the desired properties. This solution is poured into a stirring aqueous surfactant solution and the resulting nanoparticle suspension is stirred under vacuum to evaporate the organic solvents. The nanosuspension is then passed though a 1.0 lm filter and the nanoparticles washed and isolated by repeated ultracentrifugation.

Example 5

Nanoparticle Characterization

The DNA-containing nanoparticles are thoroughly characterized for their particle size distribution, supercoiled DNA content, encapsulation efficiency, and surface compositions. The instruments required for the characterization are available either in our laboratory or departmental facilities. The particle size distribution of the DNA-containing nanoparticles is determined by quasielastic-laser light scattering (QELS) and scanning electron microscopy (SEM). The QELS provides an average particle size as well as population distribution whereas SEM provides a visual confirmation of the QELS results. To maximize the expression of an encoded gene, the supercoiled DNA content of the nanoparticles should be maximized. The ratio of supercoiled DNA to the nicked and linear DNA is determined using agarose gel electrophoresis as described. The nanoparticles are dissolved in dichloromethane and the plasmid DNA extracted with TRIS/EDTA buffer with gentle shaking. The aqueous phase is removed, extracted gently with dichloromethane (to remove all polymer) then electrophoresed on a 1% agarose gel. The supercoiled DNA vs. linear and nicked DNA ratio is determined using a Gel Doc apparatus by integrating the intensity of each DNA band as a volume, then determining the contribution of the supercoiled DNA band to the total band intensities. The encapsulation efficiency of the nanoparticles is determined using a fluorometric Picogreen assay. Picogreen (Molecular Probes, Eugene, Oreg.) is a reagent that is fluorescent when intercalated with double stranded DNA. The content of DNA in each sphere preparation is then determined by dissolving the nanoparticles in dimethyl sulfoxide (DMSO) followed by selective precipitation of the polymer in buffer. The remaining plasmid DNA solution is incubated with Picogreen then quantitated by fluorimetry according to a plasmid standard curve. The surface composition of the nanoparticles is determined using X-Ray Photoelectron Spectroscopy (XPS) as previously described (Putnam et al., 8th International Symposium on Recent Advances in Drug Delivery Systems, Feb. 24–27, 1997, pp. 258–259). The surface composition is important to determine if DNA is adsorbed on the surface of the nanoparticle rather than encapsulated within the hydrophobic polymer matrix.

What we claim is:

1. An endosomal lysing polymer comprising
   at least one hydrolyzable functional moiety selected from the group consisting of ortho-esters, hydrazones, and cis-acetonyls, wherein an endosomal lysing agent is released upon hydrolysis of the hydrolyzable functional moiety; and
   at least one ionizable functional moiety, wherein the ionizable functional moiety comprises a proton acceptor site and is operably linked to the hydrolyzable functional moiety;
wherein said polymer is capable of effecting the lysis of an endosome in response to a change in pH.

2. The endosomal lysing polymer of claim 1 is a biocompatible polymer.

3. The endosomal lysing polymer of claim 1 is a biodegradable polymer.

4. The endosomal lysing polymer of claim 1 is a biocompatible and biodegradable polymer.

5. The endosomal lysing polymer of claim 1, wherein the hydrolysis of said one or more hydrolyzable functional moieties effects a hydrophobic/hydrophilic transition of said polymer.

6. The endosomal lysing polymer of claim 5, wherein said hydrolysis further effects the release of an endosomolytic agent capable of disrupting lipid bilayers.

7. The endosomal lysing polymer of claim 1, wherein the ionizable functional moiety comprises a nitrogen atom.

8. The endosomal lysing polymer of claim 1, wherein the ortho-ester is selected from the group consisting of N-[2-methyl-1,3-O-ethoxyethylidine-propanediol] methacrylamide, ortho-ester derivatives of tartaric acid, ortho-ester derivatives of threitol, and ortho-ester derivatives of dithiothreitol.

9. The endosomal lysing polymer of claim 1, wherein the polymer is combined in a form selected from the group consisting of:
   mixed polymers;
   linear co-polymers;
   branched co-polymers; and
   dendrimer branched co-polymers.

10. The endosomal lysing polymer of claim 1, wherein said polymer is further functionalized with a targeting agent selected from the group consisting of low density lipoproteins, transferrin, asiaglycoproteins, gp120 envelope protein of human immunodeficiency virus, antibodies and carbohydrates.

11. The endosomal lysing polymer of claim 1, wherein the endosomal lysing agent is ethanol.

12. The endosomal lysing polymer of claim 1, wherein the hydrolyzable functional moiety is an ortho-ester.

13. The endosomal lysing polymer of claim 1, wherein the hydrolyzable functional moiety is a hydrazone.

14. The endosomal lysing polymer of claim 1, wherein the hydrolyzable functional moiety is a cis-acetonyl.

15. The endosomal lysing polymer of claim 1, wherein the ionizable functional moiety is an imidazole group.

16. A cell delivery composition comprising:
   a compound to be delivered to a cell;
   a delivery agent bound to the compound; and
   the endosomal lysing polymer of claim 1.

17. The cell delivery composition of claim 16, wherein the compound to be delivered to a cell is selected from the group consisting of anti-AIDS substances, anti-cancer substances, antibiotics, immunosuppressants, anti-viral substances, enzyme inhibitors, neurotoxins, opioids, hypnotics, antihistamines, lubricants, tranquilizers, anti-convulsants, muscle relaxants, anti-Parkinson substances, antispasmodics and muscle contractants, miotics, anticholinergics, anti-glaucoma compounds, anti-parasite compounds, anti-protozoal compounds, anti-hypertensives, analgesics, anti-pyretics, anti-inflammatory agents, local anesthetics, ophthalmics, prostaglandins, anti-depressants, anti-psychotic substances, anti-emetics, imaging agents, specific targeting agents, neurotransmitters, proteins, cell response modifiers, vaccines, anti-sense agents, RNA and ribozymes.

18. A biocompatible composition comprising:
   a packaging agent, characterized by an ability to bind to a therapeutic agent and mediate import into endosomes; and
   an endosomal lysing polymer comprising
      at least one hydrolyzable functional moiety selected from the group consisting of ortho-esters, hydrazones, and cis-acetonyls, wherein an endosomal lysing agent is released upon hydrolysis of the hydrolyzable functional moiety; and
      at least one ionizable functional moiety, wherein the ionizable functional moiety comprises a proton acceptor site and is operably linked to the hydrolyzable functional moiety:
   wherein said polymer is capable of effecting the lysis of an endosome in response to a change in pH.

19. The biocompatible composition of claim 18, wherein said packaging agent and said endosomal lysing polymer are combined in a form selected from the group consisting of:
   mixed polymers;
   linear co-polymers;
   branched co-polymers; and
   dendrimer branched co-polymers.

20. The biocompatible composition of claim 18, wherein said therapeutic agent comprises a nucleic acid.

21. The biocompatible composition of claim 18, wherein the packaging agent associates with the therapeutic agent through a covalent interaction.

22. The biocompatible composition of claim 28, wherein the packaging agent associates with the therapeutic agent through a non-covalent interaction.

23. The composition of claim 20, wherein the packaging agent condenses the nucleic acid.

24. The composition of claim 20, wherein the packaging agent condenses the nucleic acid to a size less than 150 nm.

25. The composition of claim 18, wherein the packaging agent comprises a material with high charge density.

26. The composition of claim 25, wherein said packaging agent comprises a tertiary amine or a quaternary amine.

27. The composition of claim 26, wherein said packaging agent is selected from the group consisting of 2-[dimethylamino]ethyl methacrylate, (3-aminopropyl) methacrylamide, 2-aminoethyl methacrylamide, aspartic acid, glutamic acid and polymers thereof.

28. The composition of claim 18, wherein the hydrolysis of said one or more hydrolyzable functional moieties effects a hydrophobic/hydrophilic transition of said polymer.

29. The composition of claim 18, wherein said hydrolysis further effects the release of an endosomolytic agent capable of disrupting lipid bilayers.

30. The biocompatible composition of claim 18, wherein the endosomal lysing agent is ethanol.

31. A method of lysing an endosome, the method comprising the steps of:
providing a composition for endosomal uptake into the cell; and
contacting the composition with the cell in the presence of an endosomal lysing polymer comprising
at least one hydrolyzable functional moiety selected from the group consisting of ortho-esters, hydrazones, and cis-acetonyls, wherein an endosomal lysing agent is released upon hydrolysis of the hydrolyzable functional moiety; and
at least one ionizable moiety, wherein the ionizable functional moiety comprises a proton acceptor site and is operably linked to the hydrolyzable functional moiety;
wherein said polymer is capable of effecting the lysis of an endosome in response to a change in pH.

32. A method for introducing a nucleic acid into a cell or a subcellular component, the method comprising the steps of:
providing a biocompatible delivery composition comprising:
a packaging agent;
an endosomal lysing polymer comprising
at least one hydrolyzable functional moiety selected from the group consisting of ortho-esters, hydrazones, and cis-acetonyls, wherein an endosomal lysing agent is released upon hydrolysis of the hydrolyzable functional moiety; and
at least one ionizable functional moiety, wherein the ionizable functional moiety comprises a proton acceptor site and is operably linked to the hydrolyzable functional moiety;
wherein said polymer is capable of effecting the lysis of an endosome in response to a change in pH; and
a nucleic acid; and
contacting the composition with cells.

33. The method of claim 32, further comprising contacting the composition with cells in the absence of a known endosomal lysing component selected from the group consisting of chloroquine, polyethyleneimine, fusogenic peptides, inactivated adenoviruses and combinations thereof.

34. The method of claim 31 or 32, wherein the endosomal lysing agent is ethanol.

* * * * *